(12) United States Patent
Steuerwald et al.

(10) Patent No.: US 7,339,178 B2
(45) Date of Patent: Mar. 4, 2008

(54) DEVICE FOR THE PHOTOMETRIC MEASUREMENT OF THE CONTENT OF A CHEMICAL SUBSTANCE IN AN ANALYTE

(75) Inventors: Ralf Steuerwald, Welzheim (DE); Matthias Knoedler, Fellbach (DE)

(73) Assignee: Endress + Hauser Conducta Gesellschaft fur Mess-u. Regeltechnik mbh + Co. KG, Gerlinge (DE)

(*) Notice: Subject to any disclaimer, the term of this patent is extended or adjusted under 35 U.S.C. 154(b) by 0 days.

(21) Appl. No.: 10/517,779

(22) PCT Filed: Jun. 3, 2003

(86) PCT No.: PCT/EP03/05768

§ 371 (c)(1),
(2), (4) Date: Sep. 12, 2005

(87) PCT Pub. No.: WO2004/003524

PCT Pub. Date: Jan. 8, 2004

(65) Prior Publication Data

US 2006/0091319 A1    May 4, 2006

(30) Foreign Application Priority Data

Jun. 28, 2002  (DE) ............................ 102 28 929

(51) Int. Cl.
*G01J 1/42* (2006.01)

(52) U.S. Cl. .................................................. 250/373
(58) Field of Classification Search ................. 250/373
See application file for complete search history.

(56) References Cited

U.S. PATENT DOCUMENTS

| 4,627,284 | A | * | 12/1986 | Gersh et al. | ............. | 73/335.01 |
| 4,873,470 | A | * | 10/1989 | Myers | ......................... | 315/240 |
| 5,745,243 | A | * | 4/1998 | Wilcox et al. | ............... | 356/419 |

* cited by examiner

*Primary Examiner*—David Porta
*Assistant Examiner*—Mindy Vu
(74) *Attorney, Agent, or Firm*—Bacon & Thomas, PLLC (57) ABSTRACT

A device for photometric measurement of the concentration of a chemical substance in a solution, including: a lamp, which emits electromagnetic radiation in a predetermined wavelength range; a first receiving unit in a measuring branch (MB), which receives the radiation transmitted through the solution at a first wavelength; a second receiving unit in a reference branch (RB), which receives the radiation transmitted through the solution at a second wavelength; and a control/evaluation unit, which, depending on the conditions present at the measuring site, uses the intensity values determined either by the measurement branch (MB) or by the reference branch (RB), in order to control the intensity of the radiation emitted by the lamp, such that the resulting, measured values are highly plausible.

10 Claims, 6 Drawing Sheets

DEVICE FOR THE PHOTOMETRIC MEASUREMENT OF THE CONTENT OF A CHEMICAL SUBSTANCE IN AN ANALYTE

FIELD OF THE INVENTION

The invention relates to a device for photometric measurement of the concentration of a chemical substance in a solution. Preferably the nitrate content in an aqueous solution or in a suspension is determined by means of the device of the invention. However, the invention is also optimally suited for photometric measurement of organic substances dissolved in water. In principle, the invention can be used for the detection of any dissolved substance which can be detected using a photometric measuring method.

BACKGROUND OF THE INVENTION

Known online systems for nitrate measurement or for measuring the content of organic substances are available from Endress+Hauser Conducta GmbH+Co. KG under the trademark "STAMOSENS". The present invention further develops the known state of the art.

SUMMARY OF THE INVENTION

An object of the invention is to provide a device which supplies highly reliable measured values.

This object is achieved by the device of the invention, which includes the following components: a lamp which emits electromagnetic radiation in a predetermined wavelength range; a first receiving unit in a measurement branch for receiving the radiation transmitted through the solution at a first wavelength; a second receiving unit in a reference branch for receiving the radiation transmitted through the solution at a second wavelength; a control/evaluation unit, which, depending on the conditions present at the measuring site, uses the intensity values determined either by the measurement branch or by the reference branch, in order to control the intensity of the radiation emitted by the lamp, such that the resulting measured values are highly plausible. In addition to improving the reproducibility of the obtained measured values, the invention also enables an expansion of the measuring range. In particular, the measuring range can be doubled in comparison to known techniques. Furthermore, e.g. in the case of nitrate measurement, the influence of disturbance variables, especially of organic substances, is considerably reduced.

In accordance with an advantageous embodiment of the device of the invention, both receiving units are UV-detectors. In the case of nitrate measurement, the UV-detector positioned in the measuring branch functions preferably at 214 nm—that is, near the absorption maximum of nitrate dissolved in water, while the UV-detector arranged in the reference branch functions preferably at 254 nm. The latter wavelength corresponds to the SAC-measurement known from DIN 38404.

An advantageous form of embodiment of the device of the invention provides that the control/evaluation unit controls the intensity of the lamp, such that at least one of the two intensity values measured in the measuring branch or in the reference branch lies within the acceptable measuring range of the respective receiving unit.

Considered to be especially favorable is the embodiment in which, in the case of a high concentration of the substance in the solution, the control/evaluation unit uses the intensity values obtained in the reference branch for controlling the intensity of the lamp, while in the case of a low concentration of the substance in the solution, the control/evaluation unit uses the intensity values obtained in the measuring branch for controlling the intensity of the lamp. Through this embodiment, a doubling of the measuring range is achieved.

Subsequently, in a further step of the process, the control/evaluation unit checks whether at least one of the two intensity values—that is, the intensity value measured in the reference branch or that measured in the measuring branch—is at least as big as a predetermined maximum intensity value.

Accordingly, the control evaluation unit checks whether the intensity value measured in the reference branch is greater than the predetermined maximum intensity value. For the case that the intensity value measured in the reference branch is greater than the predetermined maximum intensity value, the control/evaluation unit controls the intensity of the lamp in predetermined steps successively downwards, until the intensity value measured in the reference branch is smaller than the predetermined maximum intensity value.

For the case that neither the intensity value measured in the reference branch nor that measured in the measuring branch is at least as great as the predetermined maximum intensity value, the control/evaluation unit increases the intensity of the lamp by a predetermined value. Subsequently, the control/evaluation unit checks whether the intensity value measured in the reference branch is greater than the predetermined maximum intensity value. For the case that the intensity value measured in the reference branch is greater than the predetermined maximum intensity value, the intensity of the lamp is decreased in predetermined steps successively until the intensity value measured in the reference branch is smaller than the predetermined maximum intensity value.

The lamp is preferably a flash lamp, in particular a xenon or deuterium flash lamp. As energy storage for supplying the lamp with a predetermined energy, preferably a first capacitor is provided, by way of which the control/evaluation unit controls the intensity of the lamp. In order to increase the intensity of the lamp, preferably a second capacitor is added to the first capacitor.

In accordance with a preferred embodiment of the device of the invention, the possibility is provided that the control of the intensity of the lamp can be deactivated. Furthermore, a preferred embodiment of the device of the invention provides that the control/evaluation unit furnishes a measured value for the concentration of the substance in the solution, based on the intensity values measured in the measuring branch and in the reference branch. Especially in this connection, it is provided that the control/evaluation unit subjects an obtained, measured value to a plausibility check, whereby it reviews the obtained intensity values at predetermined conditions; subsequently, the control/evaluation unit assigns a disturbance variable, found as a result of the plausibility check, to an obtained measured value. Measured value and, if present, the disturbance variable are shown on a display. Through this, the operator is given the opportunity to take appropriate countermeasures.

A preferred form of embodiment of the device of the invention provides that the control/evaluation unit statistically determines a measured value based on a plurality of individual, measured values. Through this, the known advantages can be realized such that short-term fluctuations have no influence on the issued measured value and the possibly present disturbance value.

The invention will now be described in greater detail on the basis of the drawings, the figures of which show as follows:

DESCRIPTION OF THE PREFERRED EMBODIMENTS

Figure 1:
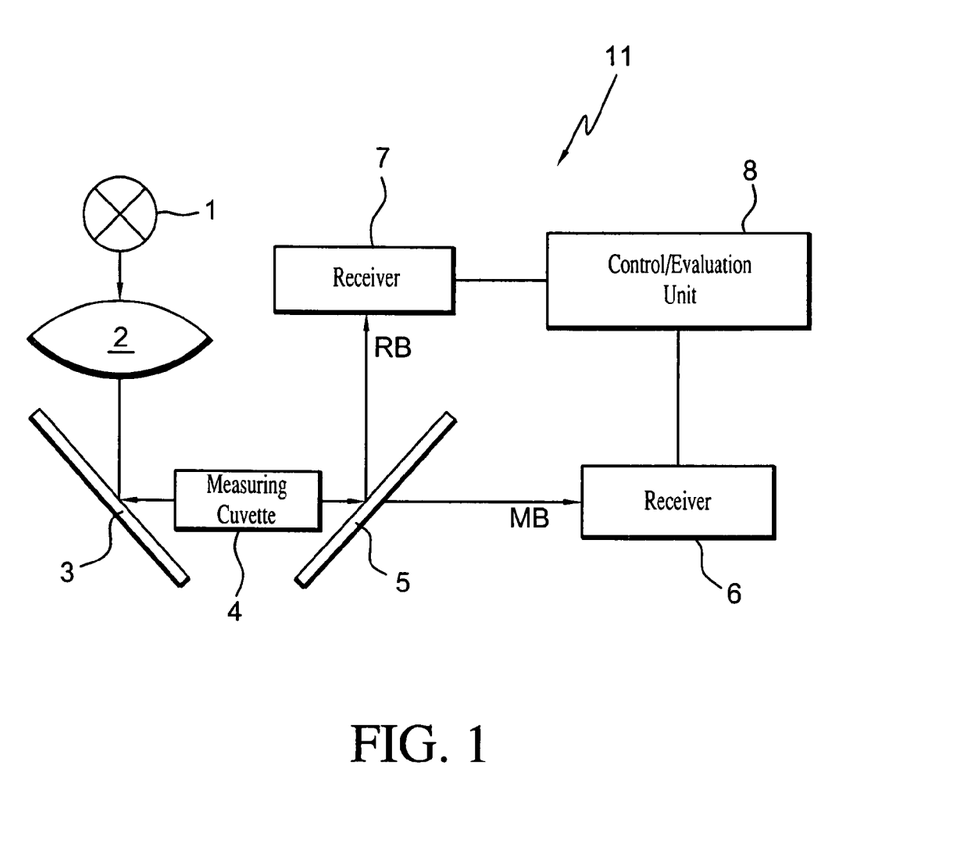
FIG. 1 is a schematic representation of an embodiment of the device of the invention.

FIG. 1 shows a schematic representation of the probe 11 of the device of the invention. In the following, a nitrate probe is referenced by way of example. However, it is understood that the probe 11 of the invention is suitable for all substances whose concentration in an aqueous solution or in a suspension can be determined using a photometric measurement. The above-mentioned substances can be, for example, organic substances.

Probes providing an online measurement of nitrate or organic substances are available from Endress+Hauser Conducta GmbH+Co. KG under the trademark "STAMOSENS" in various embodiments.

A nitrate probe 11 works on the principle that nitrate has a significant absorption peak in the UV-region. The amplitude of the absorption peak depends on the nitrate concentration of the solution. For determining the nitrate concentration, the nitrate probe 11 penetrates the aqueous solution, or slurry, as the case may be. The solution is located in the measuring duct or in the measuring cuvette 4. Using a broadband light source, for example a xenon or deuterium flash lamp, plane-parallel light is radiated through the solution. The light emitted from the flash lamp 1 lies preferably in a wavelength range of circa 180-2000 nm. The alignment into parallel light is accomplished via the condensing lens 2; the deflection of the light from the condensing lens 2 to the measuring cuvette 4 arranged perpendicularly to it is accomplished using a light-deflecting mirror 3.

In passing through the solution, the light is weakened in characteristic wavelength ranges. The transmitted light is split by a beam splitter 5 into two light branches perpendicular to one another, into the measuring branch MB and into the reference branch RB. The beam splitter 5 is made preferably of quartz glass. The advantage of using a beam splitter 5 is that it can compensate for punctiform contaminations which then have no influence on the accuracy of the nitrate probe 11. The measuring light in the measuring branch MB is detected by the receiver 6, the reference light in the reference branch RB goes to the receiver 7. The receiver 6 detects the measuring light at 214 nm, that is, in the vicinity of the wavelength at which nitrate dissolved in water has its absorption maximum. The reference light is likewise measured in the UV-region. The wavelength preferably lies at 254 nm, that is, at a wavelength near the wavelength of the measuring light. By evaluating the measured intensities, or the voltage values representing the intensities, in the measuring branch and in the reference branch, disturbance variables which equally influence both measurements can be effectively eliminated. These disturbance variables can be, for example, fluctuations of the concentration of sulfate, chloride, turbidities, and organic substances in the solution.

The evaluation of the intensity values determined by means of the receivers 6, 7 and the calculation of the nitrate concentration present in the aqueous solution is accomplished using the control/evaluation unit 8.

Figure 2:
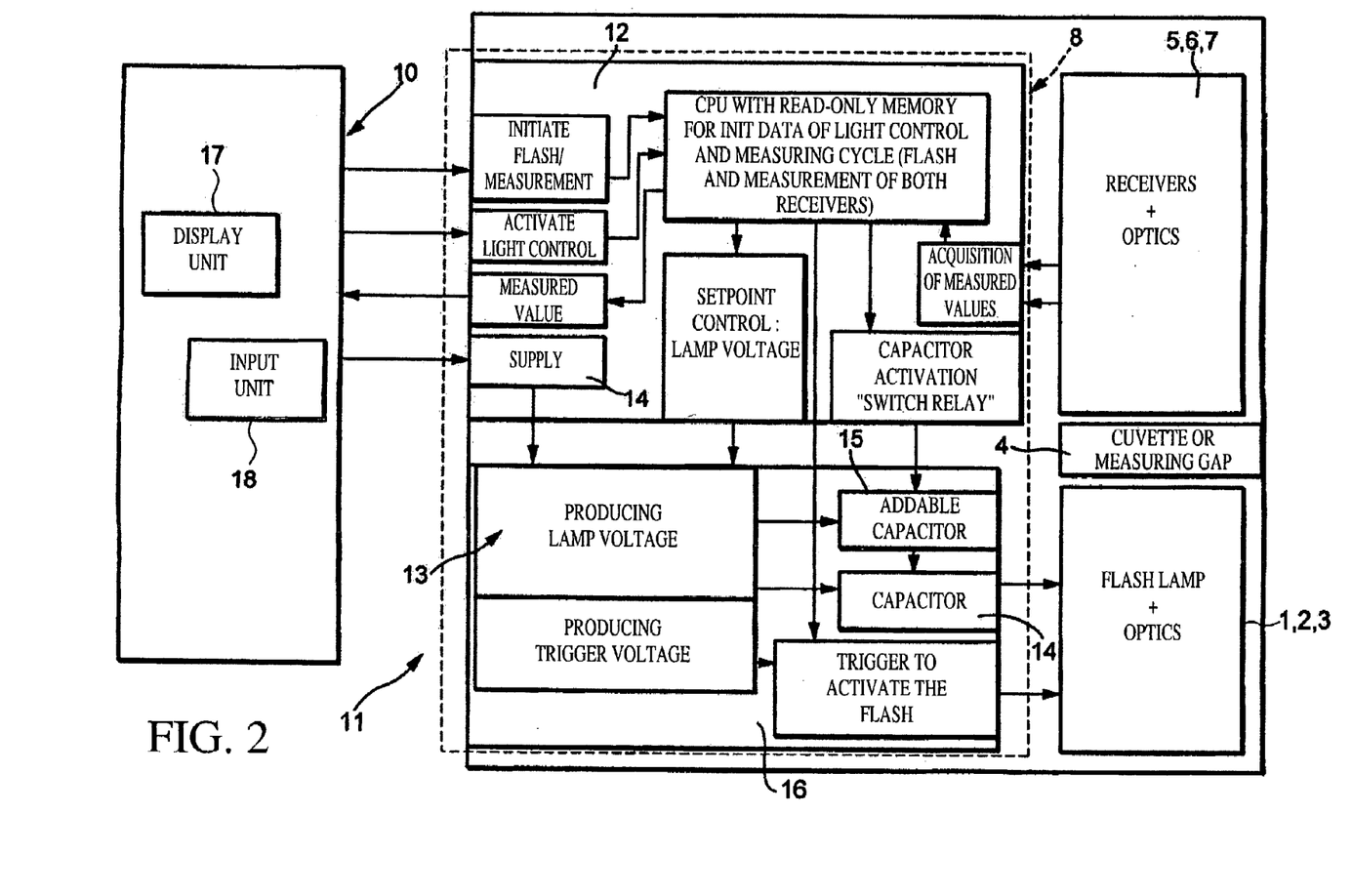
FIG. 2 is a block diagram of a preferred embodiment of the device of the invention.

FIG. 2 shows a block diagram of a preferred embodiment of a system for online nitrate measurement. The system represented in FIG. 2 is ideally suited for adjusting the intensity of the flash emitted by the flash lamp 1 to prevailing conditions at the measuring site.

The system for online nitrate measurement is composed of the nitrate probe 11 and the transmitter 10. The nitrate probe 11 includes a flash lamp 1 with associated optics, the measuring duct (or the measuring cuvette 4, as the case may be), the receivers 6, 7 and their associated optics, the high voltage power section 16, and the control/evaluation unit 8. The intensity values measured by the receivers 6, 7 are forwarded to the control/evaluation unit 8.

As previously mentioned, according to the invention, the intensity of the flash lamp 1 is controlled on the basis of the conditions at the measuring site. A software algorithm serves for this purpose. A preferred embodiment of the software algorithm is described in detail on the basis of the flow diagrams shown in the following figures: FIG. 3, FIG. 3a, FIG. 3b, and FIG. 3c. This algorithm references the intensity values detected in the reference branch and/or in the measuring branch to adjust the intensity of the flash issued by the flash lamp 1 optimally to the conditions prevailing at the measuring site. Through this, an optimized adjustment of the measuring system to the measuring task can be achieved; even large disturbance variables are able to be compensated. Furthermore, a reproducible measurement can be achieved through the use of a measuring branch and a reference branch.

In the illustrated example of an embodiment, the measured values supplied by the probe 11 are statistically evaluated in the transmitter 10 and presented to the operator via a display 17. Furthermore, data which give information concerning the reliability and/or plausibility of the measured values are made available to the operator. In addition, the transmitter 10 has an input unit 18. A transmitter 10 preferably used in connection with the invention is available from Endress+Hauser Conducta GmbH+Co. KG under the trademark "STAMOSENS CNM 750".

The flow diagrams illustrated in FIG. 3, FIG. 3a, FIG. 3b, and FIG. 3c describe a preferred embodiment of the software algorithm, by way of which the control/evaluation unit 8 controls the lamp intensity. The measuring range of the nitrate probe 11 is determined by two limiting, measured values depending on the particular receivers 6, 7 and the circuit arrangement: if the intensity values exceed a maximum allowable intensity value $I_{max}$, then the receiver 6, 7 becomes overdriven; if the measured intensity value lies below a minimum intensity value $I_{min}$, then the measured value disappears in the noise. In the known solutions, the lamp intensity is always controlled such that, in the reference branch, an intensity value is detected that remains as constant as possible; the intensity in the measuring branch then changes depending on the nitrate concentration of the solution.

According to the invention, depending on the conditions existing at the measuring site, either the intensity value in the reference branch or the intensity value in the measuring branch is used for controlling the intensity of the flash lamp 1. Especially in the case of a high nitrate concentration, the intensity value in the reference branch is also still relevant for light control; however, in the case of a low nitrate concentration, the intensity value in the measuring branch is referenced for controlling the light of the flash lamp 1.

Figure 3:
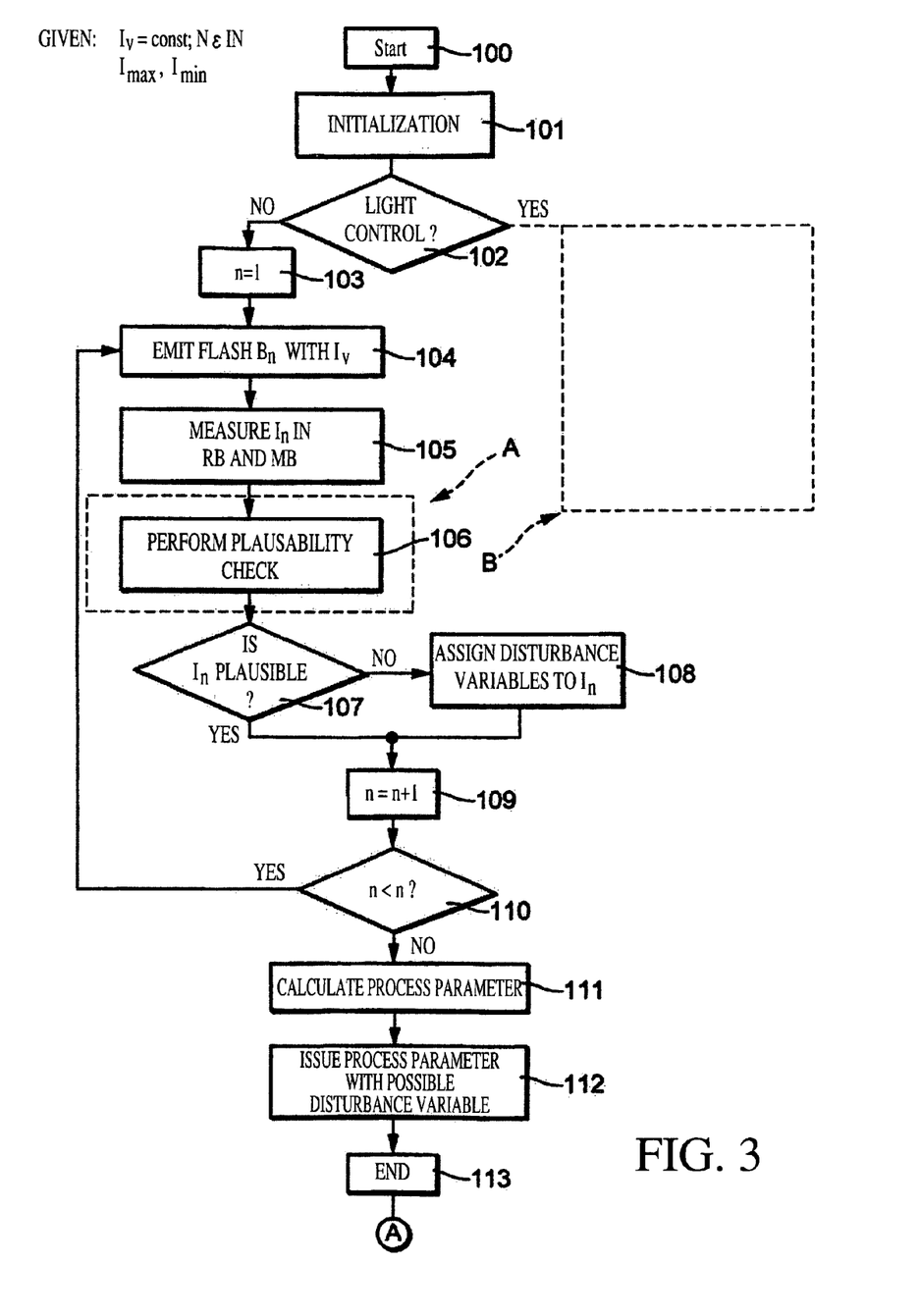
FIG. 3 is a flow diagram for the operation of the control/evaluation unit of FIG. 2.

The flow diagram illustrated in FIG. 3 will now be described. The program start occurs at point 100. At 101, the initialization of the microprocessor 12 takes place. Preferably the initialization data are entered in a read only memory assigned to the microprocessor 12. These data concern the measuring cycle and the light control of the flash lamp 1. Especially, the intensity $I_v$ of a light flash of the flash lamp 1, the number N of flashes B needed for the statistical calculation of a measured value, as well as the maximum intensity value $I_{max}$ and the minimum intensity value $I_{min}$ of the receivers 6, 7 are predetermined. At point 102 the microprocessor 12 receives the information on whether or not a light control should occur. If the light control is not activated, then, at program point 103, a counter is set to 1. Subsequently, the program steps 104 to 110 are run through N times.

At program point 104, a light flash B with the intensity $I_v$ is emitted from the flash lamp 1. At point 105, the intensity of the light flash is detected by the receivers 6, 7 in the reference branch RB and in the measuring branch MB. At 106, a plausibility check is carried out (note also box A in FIG. 3). The program points 114 to 117, which are run through successively at the plausibility check 106, are illustrated separately in FIG. 3a in the detailing of box A. At point 114, it is checked whether the measured intensity in the measuring branch MB or that in the reference branch RB is greater than the predetermined maximum intensity value $I_{max}$. If either the measured value in the measuring branch MB or that in the reference branch RB fulfills this condition, then, at the program points 107, 108, the corresponding measured value is provided with the marker "Disturbance Variable: Light Intensity." In plain language, this means that the intensity $I_v$ of the light flash of flash lamp 1—for whichever reasons—is too high, and that the corresponding measured value is, therefore, not plausible.

Figure 3A:
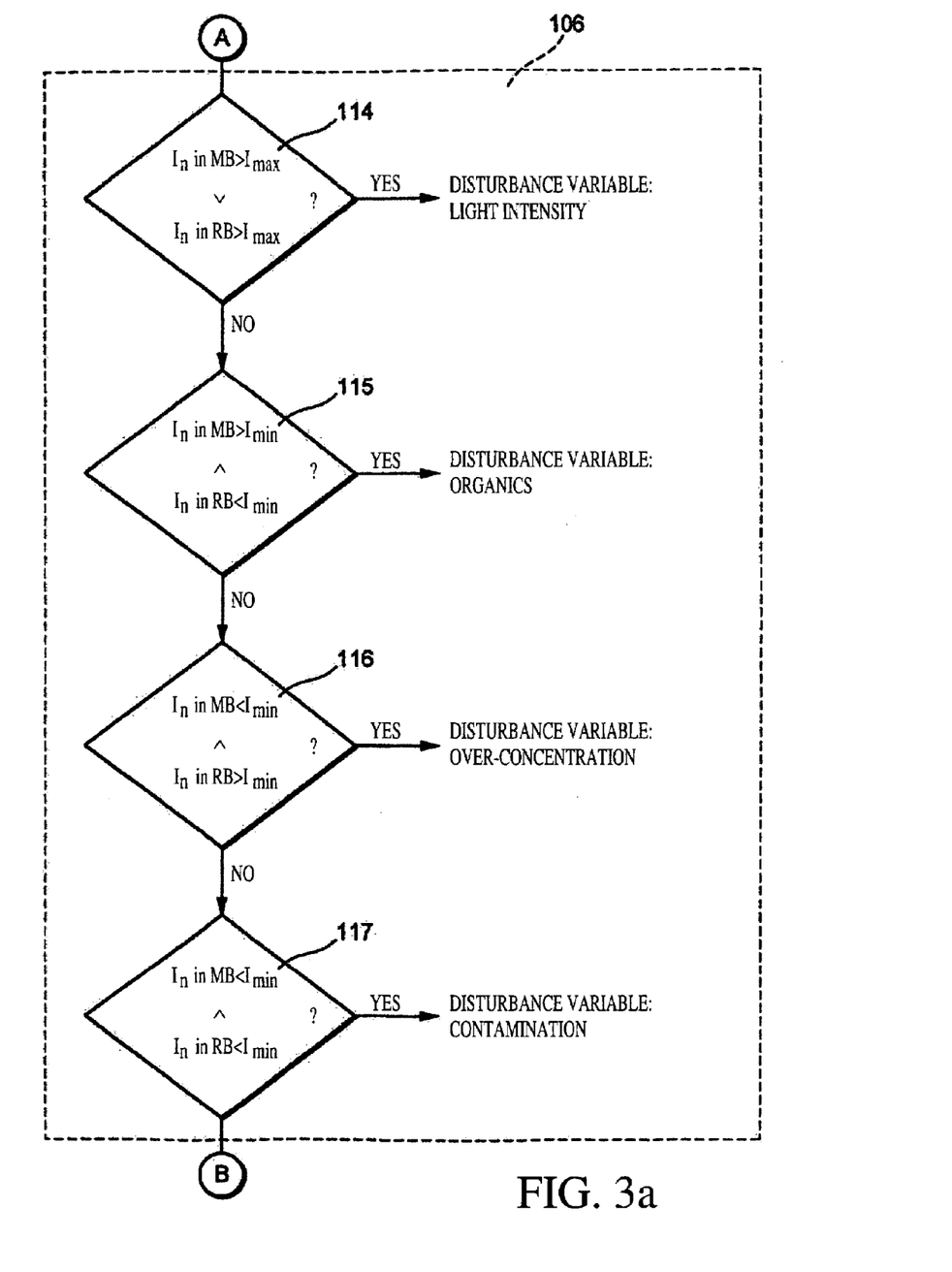
FIG. 3a is a flow diagram for the plausibility check 106 at box A in FIG. 3.

If the maximum intensity value $I_v$ is exceeded neither in the measuring branch MB nor in the reference branch RB, then, at point 115, it is checked whether the intensity value in the measuring branch MB is greater than the predetermined minimum intensity value $I_{min}$, and whether the intensity value in the reference branch RB is smaller than the predetermined minimum intensity value $I_{min}$. If this condition is fulfilled, then, at the program points 107, 108, the corresponding measured value is provided with the marker "Disturbance Variable: Organics," which means that the concentration of organic substances in the solution has exceeded an allowable degree. For this reason, a sufficiently exact determination of the nitrate concentration in the aqueous solution, or in the suspension, as the case may be, is no longer possible—the plausibility of the obtained measured value is thus called into question.

If neither the condition given at point 114, nor that given at point 115, is fulfilled, then, at point 116, it is checked whether the intensity value in the measuring branch MB is smaller than the predetermined minimum intensity value $I_{min}$, and whether the intensity value in the reference branch RB is larger than the predetermined minimum value $I_{min}$. If this condition is fulfilled, then, at the program points 107, 108, the corresponding measured value is provided with the marker "Disturbance Variable: Over-Concentration," which means that concentration of nitrate in the aqueous solution or in the suspension has exceeded the reliably measurable maximum value.

If none of the disturbance variables monitored at the points 114, 115, 116 can be identified, then, at program point 117, a test is conducted to identify a fourth disturbance variable: Contamination. Here it is checked whether the intensity value in the measuring branch MB and the intensity value in the reference branch RB are smaller than the predetermined minimum intensity value $I_{min}$. If this condition is fulfilled, then, at the program points 107, 108, the corresponding measured value is provided with the marker "Disturbance Variable: Contamination," which means that the contamination in the solution makes a reasonable nitrate measurement impossible.

For generating a measured value which will then finally be displayed on the display unit 17, N-measured values are used, and statistically evaluated (point 111). If only a small number of the N-measured values are designated as not plausible, then the process parameter, namely the nitrate concentration, is calculated and displayed (point 112). If the number of not-plausible measured values lies above a predetermined limit value, then likewise the measured value is calculated (point 111), but it is issued with the corresponding marker provided (point 113). It is then left to the operator to take an appropriate measure in order to counteract the disturbance variable. In the case of the disturbance variable: Light Intensity, the measure could be a replacement of the flash lamp 1.

A far more effective possibility of compensation exists in the activation of the lamp control of the invention (program point 102). The activation can be accomplished e.g. manually through a corresponding keyed entry at the input unit 18. The individual program steps are given in FIGS. 3b and 3c.

Figure 3B:
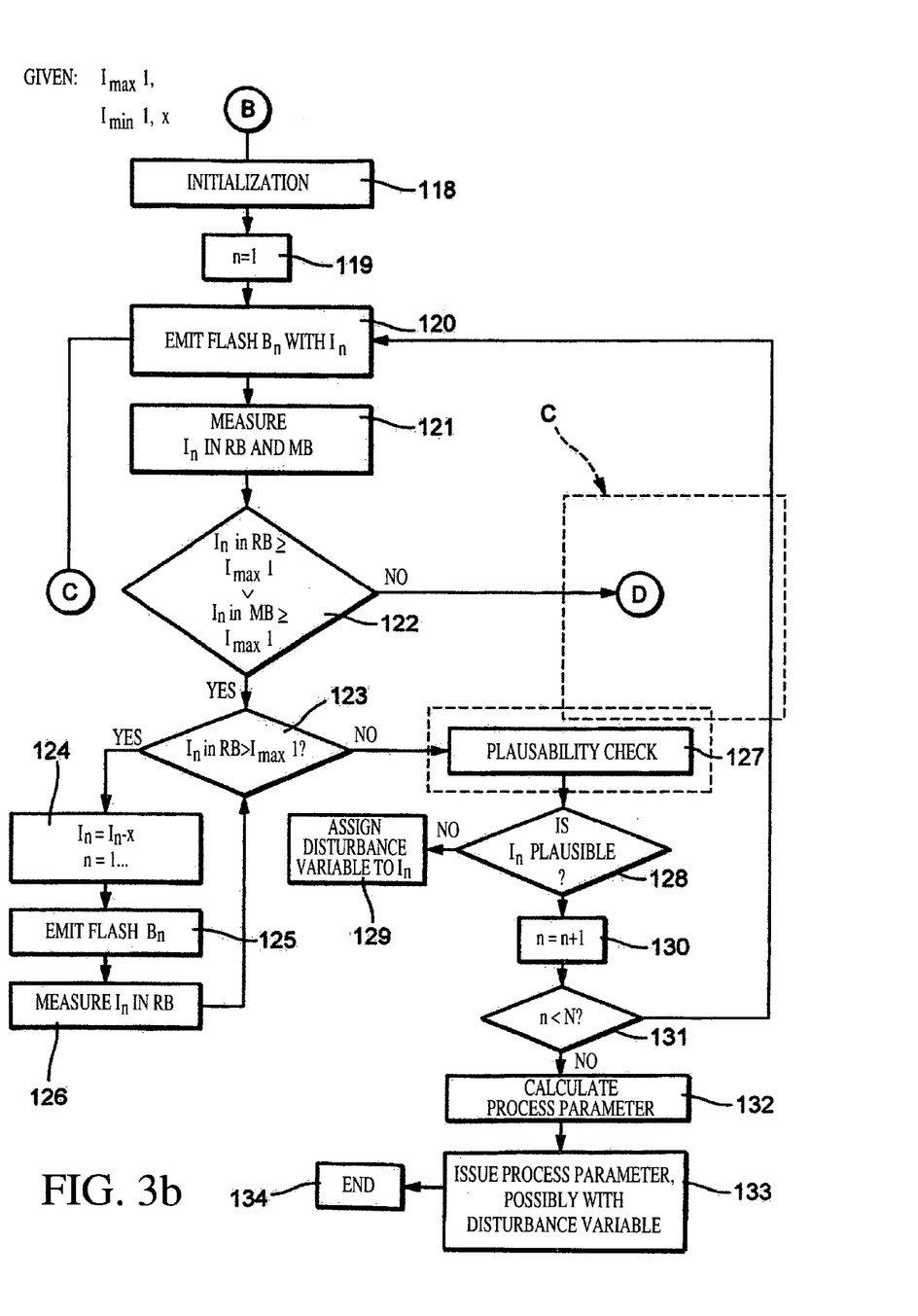
FIG. 3b is a flow diagram for option B in FIG. 3.

The initialization of the microprocessor 12 is in turn accomplished at program point 118. At 119 a measuring cycle is started. The program steps 120 to 131 are subsequently run through N-times in a loop. At 120, the flash lamp 1 emits a light flash B with the intensity $I_v$. After the radiation passes through the medium, the intensity of the light flash is detected by the receivers 6, 7 in the reference branch RB and in the measuring branch MB (point 121). At point 122, it is checked whether the intensity value in the reference branch RB or whether the intensity value in the measuring branch MB is greater than or equal to a predetermined maximum intensity value $I_{max1}$. Incidentally, the predetermined value $I_{max1}$, preferably is smaller than the predetermined value $I_{max}$ in the case of shut-off light control. If the condition named at point 121 is fulfilled, then, at point 123, it is checked whether the intensity value in the reference branch RB is greater than $I_{max1}$. If this condition is also fulfilled, then the intensity of the flash lamp is reduced by a predetermined value X. At 125, a flash is emitted and the corresponding intensity value is obtained in the reference branch RB. The loop 124, 125, 126 is run through until the condition given at point 123 is fulfilled; the cycle is run through a maximum of M-times.

As soon as the condition given at point 123 is fulfilled, at 127, the plausibility check, described in detail in connection with FIG. 2b, is conducted. In turn, a measured value based on statistical calculation is issued, potentially with the designation of a disturbance variable (points 128 to 134).

In summary, in the control illustrated in FIG. 3b, an overdriving of the receivers 6, 7 is counteracted thereby, that the light intensity of flash lamp 1 is controlled downwards in steps, until the intensity value in the reference branch RB has reached a predetermined maximum intensity value $I_{max1}$. Through this, an overdriving of the receivers 6, 7 resulting from a too-high lamp intensity can, in a variety of circumstances, be compensated for automatically.

Figure 3C:
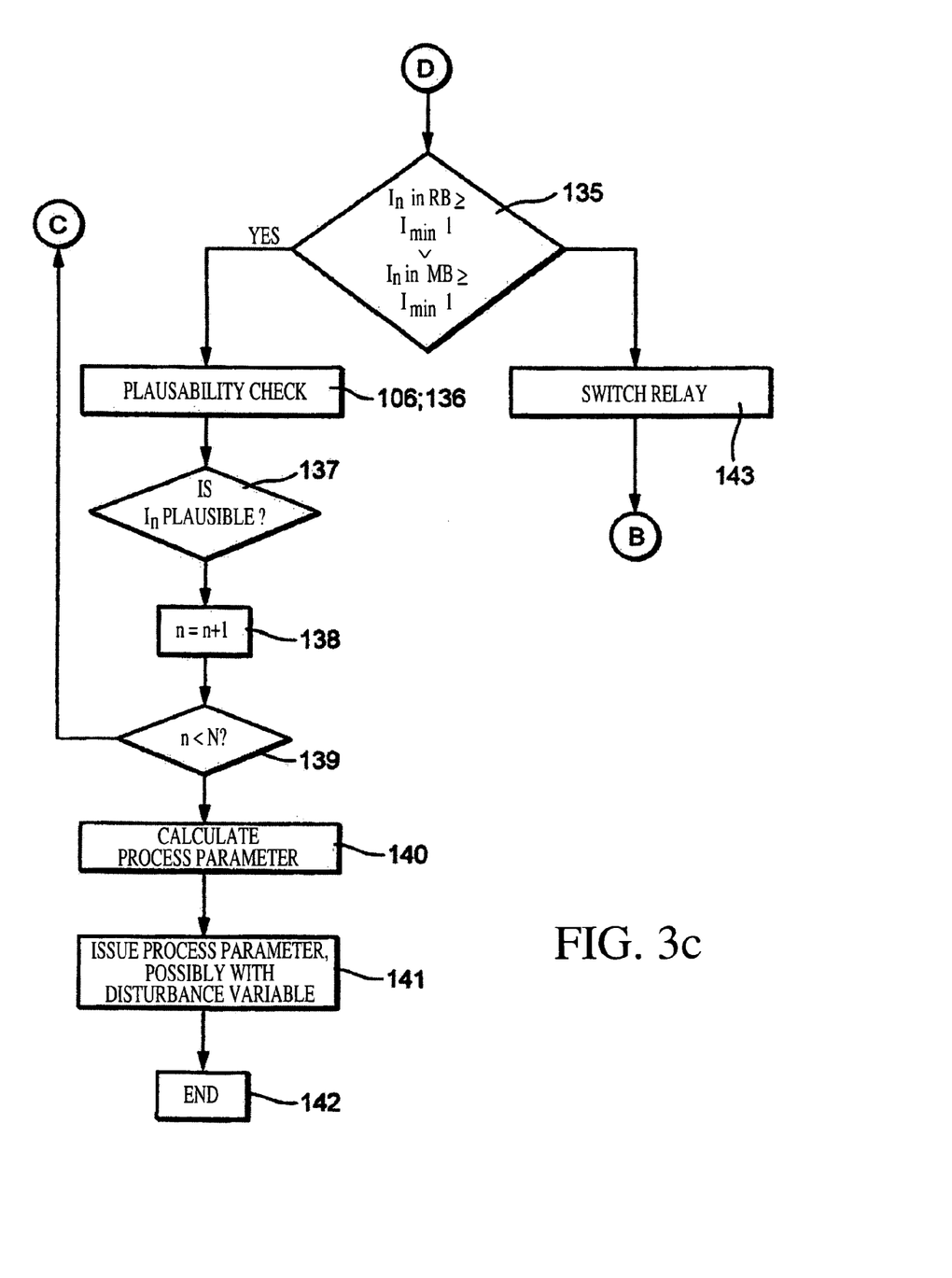
FIG. 3c is a flow diagram for option C in FIG. 3b.

If the condition obtained at program point 122 in FIG. 3*b* turns out negative—that is, neither the intensity value measured in the reference branch RB nor that in the measuring branch MB lies above the maximum intensity value $I_{max1}$—then the program jumps to point 135 in FIG. 3*c*. At point 135, it is tested whether the intensity value in the reference branch RB or that in the measuring branch MB is greater than or equal to a predetermined minimum intensity value $I_{min1}$. Note that the operating range of the probe 11 preferably lies between the minimum intensity value $I_{min1}$ and the maximum intensity value $I_{max1}$. If the condition given at point 135 is fulfilled, then the plausibility check described in FIG. 3*a* is subsequently conducted. A measured value for the process parameter is—as already described above—calculated and issued. If the condition given at point 135 is not fulfilled, then, at point 143, a second capacitor 15 is added to the capacitor 14 by connection via a relay. The intensity of the light flash of the flash lamp 1 is thereby increased, in this example in particular the intensity of the light flash is doubled. The program points already described in FIG. 3*b* are subsequently run through, that is, if necessary, the intensity of the flash lamp 1 is controlled successively downward until the intensity value in the reference branch RB lies below the predetermined maximum intensity value $I_{max1}$.

In summary, with the flash lamp light control of the invention, sufficiently reliable measured values can be obtained if at least the intensity value in the reference branch or the intensity value in the measuring branch lies in the operating range of the probe. If the nitrate content in the solution is high, then the light control is accomplished using the intensity values measured in the reference branch; if the nitrate concentration in the solution is low, then the intensity values obtained in the measuring branch are relevant for the light control. In this way, the operating range of the nitrate probe of the invention is doubled in comparison to the known techniques.

The invention claimed is:

1. A device for photometric measurement of the concentration of a chemical substance in a solution, comprising:
    a lamp, which emits electromagnetic radiation in a predetermined wavelength range and at a given intensity value;
    a first receiving unit in a measuring branch (MB), which receives the radiation transmitted through the solution at a first wavelength;
    a second receiving unit in a reference branch (RB), which receives the radiation transmitted through the solution at a second wavelength; and
    a control/evaluation unit connected to said first receiving unit and said second receiving unit, which uses the intensity values determined either by the measurement branch (MB) or by the reference branch (RB), in order to control the intensity of the radiation emitted by said lamp, such that the measured values made available are highly plausible, wherein:
    in the case of a high concentration of the substance in the solution, said control/evaluation unit uses the intensity value obtained in the reference branch (RB) to control the intensity of said lamp; and
    in the case of a low concentration of the substance in the solution, said control/evaluation unit uses the intensity value obtained in the measuring branch (MB) to control the intensity of said lamp.

2. The device as claimed in claim 1, wherein:
    said first receiving unit and said second receiving unit are UV-detectors.

3. The device as claimed in claim 1, wherein:
    said control/evaluation unit effects control in such a way that at least one of the two intensity values, measured in the measuring branch (MB) or in the reference branch (RB), lies within the measuring range of said respective receiving unit.

4. The device as claimed in claim 3, wherein:
    said control/evaluation unit checks whether one of the two intensity values—that is, the intensity value measured in the reference branch (RB) or that in the measuring branch (MB)—is at least as great as a predetermined maximum intensity value ($Imax_1$).

5. The device as claimed in claim 1, further comprising:
    a display, wherein:
    said control/evaluation unit presents the measured value and the possibly present disturbance variable on said display.

6. The device as claimed in claim 1 wherein:
    said control/evaluation unit statistically determines a measured value based on a plurality of individual, measured values.

7. A device for photometric measurement of the concentration of a chemical substance in a solution, comprising:
    a lamp, which emits electromagnetic radiation in a predetermined wavelength range and at a given intensity value;
    a first receiving unit in a measuring branch (MB), which receives the radiation transmitted through the solution at a first wavelength;
    a second receiving unit in a reference branch (RB), which receives the radiation transmitted through the solution at a second wavelength; and
    a control/evaluation unit connected to said first receiving unit and said second receiving unit, which uses the intensity values determined either by the measurement branch (MB) or by the reference branch (RB), in order to control the intensity of the radiation emitted by said lamp, such that the measured values made available are highly plausible, wherein:
    in the case of a high concentration of the substance in the solution, said control/evaluation unit uses the intensity value obtained in the reference branch (RB) to control the intensity of said lamp;
    in the case of a low concentration of the substance in the solution, said control/evaluation unit uses the intensity value obtained in the measuring branch (MB) to control the intensity of said lamp;
    said control/evaluation unit checks whether the intensity value measured in the reference branch (RB) is greater than the predetermined maximum intensity value ($Imax_1$); and
    in the case that the intensity value measured in the reference branch (RB) is greater than the predetermined maximum intensity value ($Imax_1$), said control/evaluation unit reduces the intensity of said lamp successively in predetermined steps, until the intensity value measured in the reference branch (RB) is smaller than the predetermined maximum intensity value ($Imax_1$).

8. A device for photometric measurement of the concentration of a chemical substance in a solution, comprising:
    a lamp, which emits electromagnetic radiation in a predetermined wavelength range and at a given intensity value;

a first receiving unit in a measuring branch (MB), which receives the radiation transmitted through the solution at a first wavelength;

a second receiving unit in a reference branch (RB), which receives the radiation transmitted through the solution at a second wavelength; and a control/evaluation unit connected to said first receiving unit and said second receiving unit, which uses the intensity values determined either by the measurement branch (MB) or by the reference branch (RB), in order to control the intensity of the radiation emitted by said lamp, such that the measured values made available are highly plausible, wherein:

said control/evaluation unit effects control in such a way that at least one of the two intensity values, measured in the measuring branch (MB) or in reference branch (RB), lies within the measuring range of said respective receiving unit;

said control/evaluation unit checks whether one of the two intensity values—that is, the intensity value measured in the reference branch (RB) or that in the measuring branch (MB)—is at least as great as a predetermined maximum intensity value ($Imax_1$);

in the case that neither the intensity value measured in the reference branch (RB) nor that in the measuring branch (MB) is at least as great as the predetermined maximum intensity value ($Imax_1$), said control/evaluation unit increases the intensity of said lamp, said control/evaluation unit subsequently checks whether the intensity value measured in the reference branch (RB) is greater than the predetermined maximum intensity value ($Imax_1$); and in the case that the intensity value measured in the reference branch (RB) is greater than the predetermined maximum intensity value ($Imax_1$), said control/evaluation unit reduces the intensity of said lamp successively in predetermined steps, until the intensity value measured in the reference branch (RB) is smaller than the predetermined maximum intensity value ($Imax_1$).

9. A device for photometric measurement of the concentration of a chemical substance in a solution, comprising:

a lamp, which emits electromagnetic radiation in a predetermined wavelength range and at a given intensity value;

a first receiving unit in a measuring branch (MB), which receives the radiation transmitted through the solution at a first wavelength;

a second receiving unit in a reference branch (RB), which receives the radiation transmitted through the solution at a second wavelength; and a control/evaluation unit connected to said first receiving unit and said second receiving unit, which uses the intensity values determined either by the measurement branch (MB) or by the reference branch (RB), in order to control the intensity of the radiation emitted by said lamp, such that the measured values made available are highly plausible, wherein:

control of the intensity of said lamp can be deactivated; and said control/evaluation unit furnishes a measured value for the concentration of the substance in the solution, on the basis of the intensity values measured in the measuring branch (MB) and the reference branch (RB).

10. A device for photometric measurement of the concentration of a chemical substance in a solution, comprising:

a lamp, which emits electromagnetic radiation in a predetermined wavelength range and at a given intensity value;

a first receiving unit in a measuring branch (MB), which receives the radiation transmitted through the solution at a first wavelength;

a second receiving unit in a reference branch (RB), which receives the radiation transmitted through the solution at a second wavelength; and a control/evaluation unit connected to said first receiving unit and said second receiving unit, which uses the intensity values determined either by the measurement branch (MB) or by the reference branch (RB), in order to control the intensity of the radiation emitted by said lamp, such that the measured values made available are highly plausible, wherein:

said control/evaluation unit subjects an obtained measured value to a plausibility check, in which the intensity values obtained in the measurement branch (MB) and the reference branch (RB) are checked for predetermined conditions; and said control/evaluation unit assigns to an obtained measured value a disturbance variable found in the course of the plausibility check.

* * * * *